United States Patent [19]

Elstrom et al.

[11] Patent Number: 5,895,362
[45] Date of Patent: Apr. 20, 1999

[54] TRANSDERMAL TRANSPORT USING ULTRASONIC STANDING WAVES

[75] Inventors: Tuan A. Elstrom, Lake Bluff; Eric B. Shain, Glencoe; Timothy P. Henning, Vernon Hills, all of Ill.

[73] Assignee: Abbott Laboratories, Abbott Park, Ill.

[21] Appl. No.: 08/606,109

[22] Filed: Feb. 23, 1996

[51] Int. Cl.⁶ .................... A61B 5/00; B65D 81/00
[52] U.S. Cl. ........................... 600/573; 600/584
[58] Field of Search ....................... 128/760, 770, 128/763, 632; 604/289, 290, 312, 313, 315, 316; 600/573, 574, 578, 579, 584; 601/2

[56] References Cited

U.S. PATENT DOCUMENTS

| | | |
|---|---|---|
| 4,542,751 | 9/1985 | Webster et al. .............. 604/312 |
| 5,112,300 | 5/1992 | Ureche ........................... 604/22 |
| 5,365,139 | 11/1994 | Kasuga et al. ................ 310/316 |
| 5,421,816 | 6/1995 | Lipkovker . |
| 5,458,140 | 10/1995 | Eppstein et al. ............. 128/760 |
| 5,484,398 | 1/1996 | Stoddard ......................... 604/22 |
| 5,582,586 | 12/1996 | Tachibana et al. ........... 128/760 |
| 5,617,851 | 4/1997 | Lipkovker ..................... 128/632 |
| 5,618,275 | 4/1997 | Bock ............................. 604/290 |
| 5,630,807 | 5/1997 | Joffe ............................. 604/313 |

*Primary Examiner*—Richard J. Apley
*Assistant Examiner*—Justine R. Yu
*Attorney, Agent, or Firm*—David L. Weinstein; Gregory W. Steele

[57] ABSTRACT

A process for the sampling of extracellular fluid across the skin of an animal involves establishing an ultrasonic standing wave across the skin and collecting fluid transudate. Sampling can be enhanced by combining the use of ultrasound with the application of a partial vacuum to the surface of the skin. An apparatus includes an ultrasonic transducer, a reflector and an absorbent material for collecting transudate. The apparatus can further include a pressure component for reducing hydrostatic pressure on the skin surface.

8 Claims, 1 Drawing Sheet

TRANSDERMAL TRANSPORT USING ULTRASONIC STANDING WAVES

FIELD OF THE INVENTION

The disclosure relates to the transdermal sampling of extracellular fluid. The present disclosure provides an apparatus and process for the enhanced transdermal transport of drugs or other substances using ultrasound standing waves.

BACKGROUND OF THE INVENTION

Conventional sampling methods for collecting body fluids typically involve invasion of the organism (e.g., physical disruption of the skin). Such invasive processes are both painful and messy. The difficulty and pain involved with the process provides a disincentive to the patient to perform the procedure.

Several techniques have been reported that involve little or minimal invasion of the skin. Exemplary such techniques are sonophoresis, iontophoresis and vacuum.

The use of iontophoresis requires using electrodes containing oxidation-reduction species as well as passing electric current through the skin. Iontophoresis has also been used to increase skin permeability. Despite the effective use of iontophoresis for skin permeation enhancement, there are problems with irreversible skin damage induced by the transmembrane passage of current.

Vacuum has been reported to draw fluid transcutaneously while avoiding the complications of invasive procedures. The use of vacuum to extract fluid across the skin is limited because of the relative impermeability of the stratum corneum.

The art discloses methods of using ultrasound traveling waves to enhance the rate of permeation of a drug medium into a selected area of contact of an individual or to enhance the rate of diffusion of a substance through the area of contact of an individual. The use of ultrasound traveling waves may induce localized skin heating.

Thus, there continues to be a need to provide a process and apparatus for sampling extracellular fluid across the skin of an animal.

The present disclosure provides ultrasonic standing waves to enhance permeation and mass transport through skin. While prior art techniques use ultrasonic traveling waves to enhance permeation of the skin, traveling waves do not enhance mass transport of the interstitial fluids. Standing waves on the other hand may promote permeation as well as mass transport. High velocity gradients exhibited by a standing wave sound field can provide enhanced mass transport specifically at boundary layer and at air-fluid interfaces within the structures of skin.

Furthermore, standing waves differ from traveling waves in radiation force. As understood in the art, radiation force is the time-average force exerted on a rigid spherical object immersed in a sound field over a number of cycles. In other words, the radiation force of a traveling wave is the gradient of the kinetic energy density minus the gradient of the potential density plus a phase factor. In contrast, the sum of the kinetic and potential energy density of a standing wave is independent of distance, and so their gradients are equal in magnitude but opposite in sign. The phase factor equals zero since it is constant with distance. Thus, the force for the standing wave is a constant times the gradient of the potential energy density whose maximum is equal to twice the potential energy density.

For example, in a traveling wave of pressure amplitude A, a particle is acted on by a small steady state force in the direction of the wave. If the wave is uniform, then the force is the same independent of the particle's position. However, in a standing wave the total pressure amplitude varies in space or position. The maximum amplitude is 2A and occurs in planes spaced at a half-wavelengths apart. The radiation force on the particle varies in both magnitude and direction. The force reverses direction every quarter wavelength.

The ratio of the maximum standing wave radiation force to the traveling wave value is approximately $(1/kR)^3$, where R is the particle radius and k is 6.28 divided by the wavelength. The wavelength in soft tissue is about $1.5/f$ millimeters, where f is the frequency in MHz (e.g. at 1 MHz the wavelength is 1.5 millimeters). If the radius of a particle is 0.01 mm and the wavelength is 1.5 mm, one obtains 0.042 for kR, 0.000073 for $(kR)^3$, and 13,600 for $(1/kR)^3$. As is apparent, the radiation force produced by a standing wave relative to a traveling wave is significant. While the radiation force is calculated for rigid spherical particles, the relationship is applicable to small biological particles such as blood cells, intracellular bodies such as chloroplasts, and mitochondria, as these cells and organelles exist in vivo, since these structures in which they are located are comparable to a suspending medium. Thus, the radiation force is applicable to biological structures existing within animal skin.

There are several advantages to the use of standing waves in enhancing skin permeability and mass transport for diagnostic sampling. First, the energy required for diagnostic sampling is less than that required for traveling wave techniques. This is evident with the fact that the radiation force generated by a standing wave is larger in comparison to a traveling wave of the same energy. Second, a standing wave using significantly less intensity but effectively producing the necessary permeability and, in addition mass transport effects, would alleviate the danger of bioacoustic effects. In addition, acoustic sources of low energy typically require less electrical power and are more amenable to miniaturization. Finally, the acoustic effect of standing waves can be localized within the stratum corneum, which is the rate-limiting barrier to transport in skin, while low frequency traveling waves tend to penetrate deeply into skin significantly beyond the stratum corneum. This can potentially cause undesirable bioeffects at bone-tissue interfaces that produce discomfort to a subject undergoing treatment, e.g., drug delivery or extracellular-fluid-extraction for diagnostic purposes.

The present disclosure provides, in part, a surface-acoustic-wave (SAW) device to generate standing waves within the stratum corneum region as a means for enhancing permeability and mass transport of analytes across the skin. A SAW device provides safe-coupling of sound field adjacent to skin since the electrodes needed to excite the waves are mounted on the opposite side of the acoustic device away from skin.

BRIEF DESCRIPTION OF THE DRAWINGS

In the drawings, which form a portion of the specification.

SUMMARY OF THE INVENTION

Figure 1:
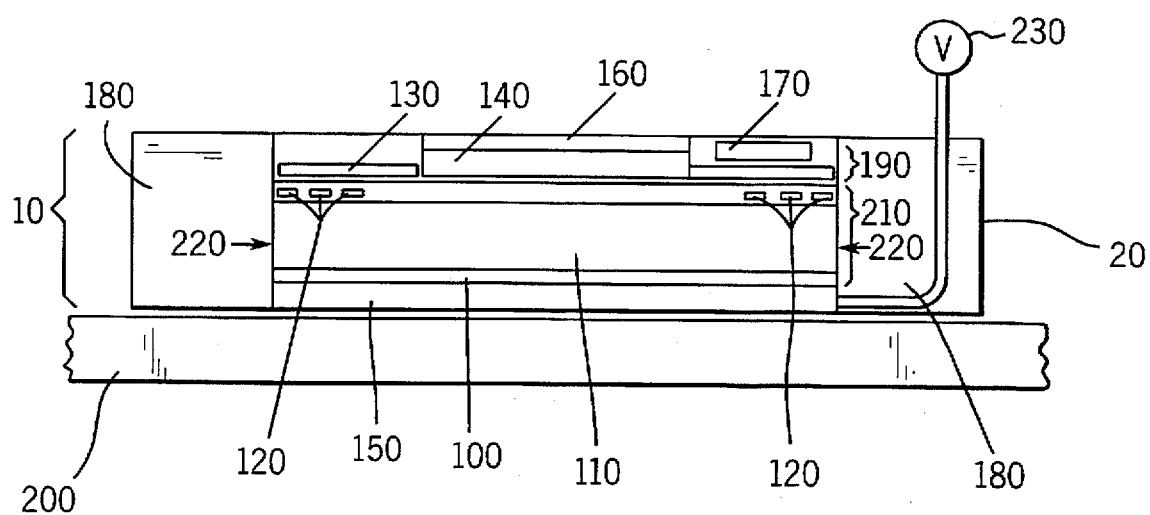
FIG. 1 illustrates one embodiment of an apparatus of the invention for the transdermal transport of extracellular fluid.

In one aspect, the present invention provides a process of sampling extracellular fluid across the skin of an animal comprising establishing an ultrasonic standing wave across the skin and collecting fluid transudate.

In a preferred process of the invention, the standing wave is generated by a surface acoustic wave device.

In alternate processes of the invention, the standing wave is established by generating an ultrasonic wave of a given wavelength from an ultrasound transducer located at a first position on the external surface of the skin and reflecting that wave from an ultrasound reflector located at a second position on the surface of the skin, wherein the half-trip distance of ultrasonic wave travel between the first and second location is equal to integer multiple number of half-wavelengths. Optionally, the pressure on the surface of the skin in the vicinity of the ultrasonic standing wave may be reduced, preferably by applying a partial vacuum to the surface of the skin.

The invention further provides an apparatus for the transdermal sampling of extracellular fluid. In a preferred apparatus of the invention, the standing wave is generated by a surface acoustic device and includes means for collecting transudate.

In alternate embodiments, the apparatus includes means for generating an ultrasonic wave through the skin of an animal, means for reflecting the ultrasonic wave sonically aligned with the means for generating the wave such that when the apparatus is positioned on the skin the half-trip distance of ultrasonic wave travel between the means for generating and the passive reflector is equal to integer multiple number of half-wavelengths, and means for collecting transudate. Optionally, the pressure on the surface of the skin in the vicinity of the ultrasonic standing wave may be reduced, preferably by applying a partial vacuum to the surface of the skin.

In preferred embodiments of this aspect of the invention, the reflector may be a passive reflector sonically aligned with the transducer such that, when the apparatus is positioned on the skin, the half-trip distance of wave travel between the transducer and the passive reflector is equal to integer multiple number of half-wavelengths. In other preferred embodiments, the reflector is a second transducer, sonically aligned with the first transducer such that, when the apparatus is positioned on the skin, the half-trip distance of ultrasonic wave travel between the two transducers satisfies the multiple number of half-wavelength resonant condition.

DETAILED DESCRIPTION

The present disclosure provides an apparatus and process for enhancing permeability and mass transport through skin, preferably the skin of a human. The apparatus comprises a device suitable to produce standing waves within the region of the stratum corneum. The process includes steps of establishing standing waves within skin and transport of compounds contained in fluid transudate to appropriately positioned sensors for detection and/or analysis of the compounds.

Any compound which can be delivered to the body through the skin or can be sampled from the body via the skin is suitable for use or detection by the processes and devices disclosed herein. Among such compounds well known in the art are compounds of clinical and/or therapeutic significance, such as glucose, cholesterol, insulin, estradiol, and other hormones or proteins, potassium, sodium, calcium, etc. The preferred compound is glucose.

As used here, the term "ultrasound" means ultrasonic radiation of a frequency above 20 kHz. Ultrasound used for most medical purposes employs frequencies ranging 50 kHz to 100 MHz.

The term "standing wave" means that acoustic wave forms exhibited within a medium remain fixed in position while the amplitude of the waves fluctuate repetituously from maximum to minimum over the total operating distance of the wave. The distance between adjacent nodes or antinodes is equal to integer multiples of half-wavelength. The phases of wave forms between two nodes or antinodes are constant.

In contrast, traveling waves have amplitudes that remain constant. A traveling acoustic wave can be characterized by a parameter of intensity. Intensity is the average power transported per unit area and is defined in a traveling acoustic wave. The intensity in a standing wave is zero.

In accordance with the present invention, ultrasound frequencies greater than 20 kHz and less than 300 MHz are preferable. The most preferable frequencies are those which, when converted to wavelengths, are comparable to single or multiples of cellular dimensions. Such frequencies will provide oscillation and mechanical motions within the fine-structure of cells and lipid-bilayers that influence movements or fluid motions within the stratum corneum.

The time period during which the standing wave is generated is typically from about 30 milliseconds to 60 minutes, more preferably from about 10 seconds to 20 minutes. The most preferred time is 30 seconds to 3 minutes.

Any type of device can be used to administer the ultrasound, which can be pulsed or continuous. The ultrasound is preferably continuous at lower frequencies and pulsed at very high frequencies to dissipate generated heat.

The preferred intensity of the applied ultrasound is less than about 5.0 W/cm$^2$, more preferably from about 0.2 to about 5.0 W/cm$^2$, and most preferably from about 0.1 to about 0.03 W/cm$^2$.

In the process of the invention, the standing wave is established by generating an ultrasonic standing wave of a given frequency and distributing the wave over the surface of the skin. The "foot print" of the ultrasonic standing wave is not critical to the invention and is typically in the form of a circular or rectangular surface area.

An ultrasonic standing wave can be established in a number of ways. One preferred apparatus capable of establishing a standing wave is a surface-acoustic-wave (SAW) device. SAWs are commercially available and are well suited for enhancing the permeation of the stratum corneum since the surface waves travel parallel to the surface and do not penetrate the skin to any significant degree, e.g., at most to about 100 micrometers. A SAW device is compact and can be constructed so as to eliminate direct electrical contact with the skin by placing the electrical contacts on a side of the device away from the skin. A SAW device is typically characterized by an electrically excited surface acoustic wave in a piezoelectric single-crystal plate substrate by use of a metallic (e.g. aluminum) interdigital transducer (IDT) structure. As is understood in the art, an IDT structure comprises a row of metallic electrodes laying parallel and adjacent, but not touching each other. Each electrode has an alternating applied voltage potential. Typical substrates are quartz, lithium niobate, and lithium tantalate, but other substrate materials are known and are suitable for use in the invention, e.g., piezoceramics such as lead-zirconate-titanate (PZT), zinc oxide (ZnO), and polyvinylidene-fluoride (PVDF). The specific operating characteristics of these materials, such as direction of particle displacement of the wave, is defined by the cut of the substrate. The anisotropy of the piezoelectric crystals allows different angles of cut with very different properties.

An alternate method of providing a standing wave is a transverse vibrating wire. The wire is secured at each end as to satisfy the standing wave resonant condition and is caused to vibrate at a desired frequency. The device is applied parallel to the skin and the field emanating from the side of the wire is used as previously described, e.g., to enhance permeation and mass transport. Structures resembling wires can also be fabricated from silicon or other suitable materials using microfabrication techniques well known in the electronic industry. Such structures can be made to operate analogous to metallic wires and can be incorporated and operated in a similar manner previously described for mating and extraction with skin.

In further embodiments, a combination of ultrasonic transducers and reflectors is arranged on the surface of a patient extremity such that the necessary spacing of multiple number of half-wavelength of ultrasonic wave to establish a standing wave is satisfied.

Single transducers can be positioned perpendicularly to the interface of different layers of skin or at the tissue-bone plane. Multiple transducers and reflectors can be positioned on the same plane. In one embodiment of a process of the invention, a transducer and a passive reflector are utilized to establish the standing wave.

In yet another embodiment of the invention, a second transducer can be used as a reflector. The two emitting transducers establish the standing wave when they are operated at the same frequency and are positioned, as is well known in the art, to satisfy the multiple number of half-wavelength resonant conditions.

As is well known in the art, the location of the transducer with respect to the reflector depends on the frequency of excitation needed to establish a standing wave via the interior of the skin. The half-trip distance of ultrasonic wave travel between the transducer and reflector should be equal to integer multiple number of half-wavelengths.

A sinusoidal voltage at a given frequency is applied to the transducer to produce an ultrasonic wave that propagates from the face of the transducer. The wave travels through the interior of the skin and exits at the reflector of the same diameter but is reflected back to the source transducer.

The half-trip distance between the transducer and reflector causes the wave to resonate and be confined between the transducer and reflector. The amplitude of the wave is controlled by the amplitude of the sinusoidal voltage signal.

As is well known, the oscillation of the transducer can be stabilized to compensate for drift using the current-voltage phase relation occurring at the resonant response of the transducer.

By changing the phases of the signals applied to each transducer, complex movement of tissues and microcirculation between tissues can occur creating more fluid flux through the skin (transudation). The transudate can then be analyzed using appropriate sensors and/or detectors. In preferred embodiments, an absorbent pad or material receives the fluid from which the content of fluid can be analyzed using appropriate sensors.

In the processes and apparatus of the invention, impedance mismatches can be reduced by applying a coupling agent to the surface of the transducer and reflector.

The coupling agent should have an absorption coefficient similar to that of water, be non-staining, non-irritating to the skin, and slow drying. It is clearly preferred that the coupling agent retain a paste or gel consistency during the time period of ultrasound administration so that contact is maintained between the ultrasound source and the skin.

Exemplary and preferred coupling agents are mixtures of mineral oil, glycerin, and propylene glycol, oil/water emulsions, and a water-based gel. A solid-state, non-crystalline polymeric film having the above-mentioned characteristics can also be used.

The description and operation of a particular embodiment of the invention maybe understood with reference to FIG. 1. As shown in FIG. 1, the device 10 includes a housing 20 which surrounds the internal mechanism and provides one or more attachment sites 180 (two shown) for fixing the device 10 to the patient's skin 200. The device 10 is configured to fit snugly on the surface of the skin. Within the device 10 is located the ultrasound source, e.g., fabricated from a thin PZT-5A piezoelectric crystal substrate 110. Typically, it is anticipated that the ultrasonic source 110 will be operating in the region of 1 to 3 MHz. Thus the thickness of a device operating at 1 MHz is approximately 0.4 mm thick. A representative area of a substrate 100 is 1 cm by 1 cm. Pairs of opposing metal electrodes 120 are deposited on the top surface of the PZT substrate. The distance between the electrodes 120 is determined by the operating frequency, in this example multiples of 2.26 mm. The metal electrodes 120 can be approximately 1 micron wide and approximately 1 mm long. Alternatively, multiple finger-interdigital electrodes (not shown) can also be utilized. In such, embodiments, the electrode fingers are typically spaced at fractions of the operating wavelength from each other and two opposing IDTs are excited by sinusoidal inputs from a function generator and power amplifier. A battery 170 powers an electronic chip 140 capable of providing memory and control functions. In addition, the electronic chip 140 can provide sinusoidal outputs amplified in an appropriate manner as an alternative to the individual generator and amplifier. A display 160 provides means by which the operation of the device, its functioning and results are provided to the user. Optionally, the device can include a port (not shown) allowing connection to an external computer and thus allowing the health care provider the ability to more closely monitor the patient's condition.

The excitation frequency of the SAW device might drift due to external conditions and operating environments. Therefore the electronic chip should contain a close-loop portion such a Phase-Lock-Loop (PLL). Since the SAW has two opposing IDTs, one of them can provide the feedback sensing input to the PLL. The chip 140 is also capable of providing a variety of other excitation functions such as square pulses. The chip 140 can also provide different modulation and phase shift functions to the SAW device. These modulation and phase shifts can provide additional bioeffects to the stratum corneum regions of the skin 200. By providing excitation to the IDTs 120, an acoustic beam is caused to propagate between the IDTs and a resulting wave is established within the region. The opposite side of PZT substrate is coated with a thin layer typically equivalent to about a one-quarter wavelength of material, typically glass 100, to maximize coupling to a coupling agent 150 between the substrate 110 and skin 200.

The coupling agent also functions as a means for transporting extracted fluids containing the compound of interest (metabolites, diffusing species, etc.) to a sensor for detection. Permeation through the coupling membrane can take place by two mechanisms; viscous flow and diffusive flow. The viscous flow mechanism can facilitate the movement of extracted transudate and the diffusive flow can facilitate the diffusion of metabolites. A hydrated polymeric membrane or hydrogel can be formulated as to have the capacity to absorb more fluid in proportion to the solid proportion of the hydrogel. A specific volume of extracted transudate can then be transported to the hydrogel for subsequent analysis by appropriate detection means. As stated above, the coupling agent medium should have a similar impedance with skin when placed between the sound source and skin in order to provide efficient transfer of acoustic energy into skin. Since the acoustic impedance of skin is similar to the impedance of water, it is assumed that the acoustic wave is propagating in water and therefore the optimal configurations and characteristics of the extraction apparatus is designed to operate with a water interface.

Optimally, the components of the device are housed in a thin molded plastic device 20, e.g., a patch. As shown in FIG. 1, the excitation or control electronic chip 140 and the batteries 170 are preferably stored within a separate compartment or layer 190 of the patch. In this way the functional elements and the control electronics can be physically separated such that the sound source is attached to the skin and the electronics are contained in small package, similar to a electronic paging devices, that can be located elsewhere near or on the body, e.g., attached to a belt. Optionally, the excitation of a SAW device 110 can be performed in a wireless fashion since the SAW is capable of receiving an excitation wave from a wave propagating through free space at specific wavelengths. In this embodiment, a separate sending unit containing electronic controls and transmitter provides the excitation wave. Preferably, the sending unit is located near the vicinity of the SAW-containing patch so as to minimize transmission requirements. The patch is attached to the surface of the skin via one or more attachment sites 180 using bioadhesives. In addition or alternatively, the patch can be further secured to the skin in the form of a bracelet or watch.

When a standing wave from the sound source is applied to the surface of skin it is physically transferred into the skin through the glass 100 and coupling agent 150 layers. While not wishing to be bound by any one theory, the penetration of the wave into the skin is limited to within a few wavelengths beyond the thickness of the stratum corneum, which is approximately 15 micrometers. It is believed that the deepest penetration is approximately 100 micrometers. As exhibited in any standing waves, cells and their constituents such as lipid-bilayers will migrate toward pressure nodes. The amplitude of displacement is determined by the elastic nature of the fine-structure of the stratum corneum. The stratum corneum will exhibit dense regions as well as regions sparse in materials. The cells in the stratum corneum such as keratenocytes that are asymmetric in shape, being long in one axis and short in another axis, will rotate to align with the preferred axis of the standing wave to minimize energy with the acoustic field. The lipid-bilayer channels between corneocytes provide regions capable of producing acoustic microstreaming near boundary layers. The microstreaming generate high velocity gradients which enhance mass transport of compounds within the extracellular fluid (ECF). The effect of the standing wave is thus to create transient intercellular pores through the stratum corneum. In conjunction with the surface standing wave, secondary standing waves are produced within the corneocytes. These secondary waves arise from flexural coupling modes of the corneocytes. Corneocytes contain approximately half water and half keratin and thus have boundaries defined by differences in densities. As material density is a parameter of the propagation of acoustic waves, velocity gradients are produced within the corneocytes which provide enhanced mass transport of ECF and subsequent intracellular permeation. The combined effect of the surface standing wave and the secondary standing wave is to produce a region of skin which exhibits enhanced permeability and convective transport of molecular species and fluids from one side of the stratum corneum to the other.

The extracellular fluid (ECF) is extracted and diffuses through the transport medium. The transport medium is then analyzed for the presence or amount of the compound of interest. Of course, the particular analytical technique utilized will be selected depending on the compound of interest, ease of use, sensitivity, etc., and other factors well known to the clinician or diagnostician. The detection and analysis can be accomplished in situ or some or all of the transport medium can be removed from the device for analysis. Several different methods are know which are suitable for use in the method and apparatus of the invention, e.g., amperometric and optical detectors.

Alternatively, a SAW device is used in the form of a mass sensor. A layer of the SAW substrate is coated with biologics, such as receptors or antibodies, reactive to ECF compounds or metabolites, and the presence of the compound is detected by changes in the SAW generated, e.g., a shift in the resonance frequency, a phase shift of the acoustic wave, or a shift in the amplitude of an acoustic wave. Since the preferred embodiments utilize a SAW device to extract ECF, it is advantageous to incorporate a portion of the substrate within a region capable of providing detection. In this embodiment, another pair of IDTs can be incorporated onto the SAW substrate in combination with a detection portion of the fluid transport/coupling medium. This portion of the fluid transport medium is coated with biologics providing specificity to the metabolites of interests. A separate set of electronic controls provides excitation of the second set of IDTs as well as detection of the frequency, phase, or amplitude shifts due to the presence of the analytes. The extraction and detection functions can operate at the same frequency or at combinations of frequencies. The spacing arrangements of the detection IDTs with respect to the operating surface provides optimal extraction and detection means. When appropriate electronics are included, the SAW device can detect the presence of increase or decrease in fluid flow by a mass sensing region and then compensate by the excitation region. Thus, such a SAW device can provide a complete system capable of controlling fluid extraction and feedback to as to optimize the ECF extraction.

Further alternate embodiments include a transducer 210, e.g., PZT sandwiched between two thin isolated electrodes, and a Reflector 220. Any passive reflector can be used in conjunction with the transducer to establish an ultrasonic standing wave. The passive reflector is positioned in the apparatus such that, when the apparatus is contacted with skin, the half-trip distance of ultrasonic wave travel between the transducer and reflector is equal to multiple of a half-wavelength.

The size of the reflector contacting the skin is preferably the same as the size of the transducer that contacts the skin.

In another embodiment, the reflector is a second transducer. The second transducer is stimulated at the same frequency as the first transducer to create a standing ultrasonic wave. The position of the second transducer in the apparatus is such that, when the apparatus is contacted with the skin, the distance separating the transducers satisfies the multiple number of half-wavelength resonant condition. Procedures for establishing such a distance are well known in the art. Of course, these embodiments also include coupling agents/fluid transport medium as previously described. Optionally, the pressure on the surface of the skin in the vicinity of the ultrasonic standing wave may be reduced, preferably by applying a partial vacuum 230 to the surface of the skins.

The present invention has been described with reference to preferred embodiments. Those embodiments are not limiting of the claims and specification in any way. One of ordinary skill in the art can readily envision changes, modifications and alterations to those embodiments that do not depart from the scope and spirit of the present invention.

What is claimed is:

1. A process of obtaining a sample of extracellular fluid across the skin of an animal comprising the steps of:
   (1) establishing an ultrasonic standing wave across the skin parallel to the surface of the skin and penetrating no more than about 100 µm, and
   (2) collecting fluid transudate.

2. The process of claim 1 wherein the standing wave is established by generating an ultrasonic wave of a given wavelength from an ultrasound transducer located at a first position on the external surface of the skin and reflecting that wave from an ultrasound reflector located at a second position on the surface of the skin, said first position being located at a distance from said second position, wherein the distance of a half-trip of ultrasonic wave travel between the first and second positions is equal to integer multiple number of half-wavelengths.

3. The process of claim 2 wherein the reflector is a passive reflector.

4. The process of claim 2 wherein the reflector is a second transducer operated at the same frequency as the transducer at the first location.

5. The process of claim 1, further comprising a step of reducing the pressure on the surface of the skin near the ultrasonic standing wave.

6. The process of claim 5 wherein a partial vacuum is applied to the surface of the skin.

7. The process of claim 1 wherein the standing wave is generated by a surface acoustic wave device.

8. The process of claim 7, further comprising a step of reducing the pressure on the surface of the skin near the ultrasonic standing wave.

* * * * *